US009309551B2

(12) United States Patent  
Charlton et al.

(10) Patent No.: US 9,309,551 B2  
(45) Date of Patent: Apr. 12, 2016

(54) ELECTRICAL DEVICES WITH ENHANCED ELECTROCHEMICAL ACTIVITY AND MANUFACTURING METHODS THEREOF

(75) Inventors: Steven C. Charlton, Osceola, IN (US); Serban Peteu, East Lansing, MI (US); Steve Sun, Tampa, FL (US); Yuan Wang, Mountain Lakes, NJ (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 173 days.

(21) Appl. No.: 13/119,228

(22) PCT Filed: Sep. 18, 2009

(86) PCT No.: PCT/US2009/057382  
§ 371 (c)(1),  
(2), (4) Date: Jul. 22, 2011

(87) PCT Pub. No.: WO2010/033748  
PCT Pub. Date: Mar. 25, 2010

(65) Prior Publication Data  
US 2012/0037921 A1   Feb. 16, 2012

Related U.S. Application Data

(60) Provisional application No. 61/098,728, filed on Sep. 19, 2008.

(51) Int. Cl.  
*H01L 21/00* (2006.01)  
*C12Q 1/00* (2006.01)  
(Continued)

(52) U.S. Cl.  
CPC ...... *C12Q 1/006* (2013.01); *C12Q 1/26* (2013.01); *G01N 27/3271* (2013.01)

(58) Field of Classification Search  
CPC ....... C12Q 1/006; C12Q 1/26; G01N 27/3271  
USPC ........................................ 438/15, 48, 49, 931  
See application file for complete search history.

(56) References Cited

U.S. PATENT DOCUMENTS

| 4,326,927 A | 4/1982 | Stetter et al. |
| 4,596,741 A | 6/1986 | Endou et al. |

(Continued)

FOREIGN PATENT DOCUMENTS

| WO | WO 2006/057722 | 6/2006 |
| WO | WO 2009/100082 | 8/2009 |

(Continued)

OTHER PUBLICATIONS

Singh et al., "SiC—C Fiber Electrode for Biological Sensing", Feb. 22, 2007, Materials Science and Engineering C, Elsevier Science SA, vol. 27, No. 3, pp. 551-557.

(Continued)

*Primary Examiner* — Jay C Kim  
(74) *Attorney, Agent, or Firm* — Dugan & Dugan, PC

(57) ABSTRACT

In some aspects, a device is provided having a member with a region of enhanced electrochemical activity. In one aspect, a sensor of enhanced electrochemical activity is provided for detecting an analyte concentration level in a bio-fluid sample. The sensor may include a sensor member of a semiconductor material wherein the sensor member has a surface region of enhanced electrochemical activity. In other aspects, the member may be made of semiconducting foam having a surface region of enhanced electrochemical activity. In some embodiments, the region may be thermally-induced. Manufacturing methods and apparatus are also provided, as are numerous other aspects.

17 Claims, 11 Drawing Sheets

(51) Int. Cl.
*C12Q 1/26* (2006.01)
*G01N 27/327* (2006.01)

(56) References Cited

U.S. PATENT DOCUMENTS

| | | | | |
|---|---|---|---|---|
| 5,338,415 | A | * | 8/1994 | Sailor et al. ............... 205/645 |
| 5,352,348 | A | * | 10/1994 | Young ............... B01J 19/0093 |
| | | | | 204/403.09 |
| 5,431,800 | A | | 7/1995 | Kirchhoff et al. |
| 5,476,776 | A | | 12/1995 | Wilkins |
| 5,593,852 | A | * | 1/1997 | Heller .................. C12Q 1/006 |
| | | | | 435/14 |
| 5,611,900 | A | | 3/1997 | Worden et al. |
| 5,627,922 | A | | 5/1997 | Kopelman et al. |
| 5,634,913 | A | | 6/1997 | Stinger |
| 5,666,353 | A | | 9/1997 | Berneth et al. |
| 5,700,695 | A | | 12/1997 | Yassinzadeh et al. |
| 5,777,372 | A | | 7/1998 | Kobashi |
| 5,866,353 | A | | 2/1999 | Berneth |
| 6,132,893 | A | * | 10/2000 | Schoning ........... G01N 27/4167 |
| | | | | 204/403.1 |
| 6,176,988 | B1 | * | 1/2001 | Kessler ................ C12Q 1/006 |
| | | | | 204/403.11 |
| 6,218,661 | B1 | | 4/2001 | Schroeder et al. |
| 6,521,109 | B1 | | 2/2003 | Bartic et al. |
| 6,521,110 | B1 | * | 2/2003 | Hodges ................ C12Q 1/004 |
| | | | | 204/403.01 |
| 6,695,958 | B1 | * | 2/2004 | Adam .................... C12Q 1/002 |
| | | | | 204/403.01 |
| 6,726,818 | B2 | * | 4/2004 | Cui ....................... C12Q 1/004 |
| | | | | 204/403.01 |
| 6,743,635 | B2 | | 6/2004 | Neel et al. |
| 7,074,519 | B2 | * | 7/2006 | Kuhr et al. .................. 429/149 |
| 7,951,632 | B1 | * | 5/2011 | Quick et al. ................. 438/46 |
| 8,202,697 | B2 | | 6/2012 | Holmes |
| 2002/0137998 | A1 | | 9/2002 | Smart et al. |
| 2002/0168290 | A1 | | 11/2002 | Yuzhakov et al. |
| 2002/0177763 | A1 | | 11/2002 | Burns et al. |
| 2003/0088166 | A1 | | 5/2003 | Say et al. |
| 2003/0212344 | A1 | | 11/2003 | Yuzhakov et al. |
| 2003/0217918 | A1 | | 11/2003 | Davies et al. |
| 2004/0002682 | A1 | | 1/2004 | Kovelman et al. |
| 2004/0039303 | A1 | | 2/2004 | Wurster et al. |
| 2004/0094432 | A1 | | 5/2004 | Neel et al. |
| 2004/0136866 | A1 | | 7/2004 | Pontis et al. |
| 2004/0146863 | A1 | | 7/2004 | Pisharody et al. |
| 2004/0200721 | A1 | | 10/2004 | Bhullar et al. |
| 2004/0254546 | A1 | | 12/2004 | Lefebvre |
| 2005/0183953 | A1 | | 8/2005 | Su et al. |
| 2005/0238537 | A1 | | 10/2005 | Say et al. |
| 2005/0261606 | A1 | | 11/2005 | Sohrab |
| 2005/0279647 | A1 | | 12/2005 | Beaty |
| 2005/0287065 | A1 | | 12/2005 | Suddarth et al. |
| 2006/0113187 | A1 | | 6/2006 | Deng et al. |
| 2006/0211933 | A1 | | 9/2006 | Zimmermann et al. |
| 2007/0027384 | A1 | | 2/2007 | Brister et al. |
| 2007/0067492 | A1 | | 3/2007 | Muraki et al. |
| 2007/0087492 | A1 | | 4/2007 | Yamanaka |
| 2007/0096164 | A1 | | 5/2007 | Peters et al. |
| 2008/0027302 | A1 | | 1/2008 | Buse et al. |
| 2008/0167578 | A1 | | 7/2008 | Bryer et al. |
| 2008/0197024 | A1 | | 8/2008 | Simpson et al. |
| 2009/0018411 | A1 | | 1/2009 | Mace et al. |
| 2010/0270150 | A1 | | 10/2010 | Wang et al. |
| 2010/0274181 | A1 | | 10/2010 | Wang et al. |
| 2010/0298679 | A1 | | 11/2010 | Wu et al. |
| 2011/0180405 | A1 | | 7/2011 | Chinnayelka et al. |

FOREIGN PATENT DOCUMENTS

| | | |
|---|---|---|
| WO | WO 2010/033660 | 3/2010 |
| WO | WO 2010/033668 | 3/2010 |
| WO | WO 2010/033741 | 3/2010 |
| WO | WO 2010/033748 | 3/2010 |

OTHER PUBLICATIONS

Isao Karube et al., "Integrated Microbiosensors for Medical Use", Dec. 1, 1989, Annals of New York Academy of Sciences, vol. 542, No. 9, pp. 470-479.
International Preliminary Report on Patentability and Written Opinion of International Application No. PCT/US2009/032991 mailed Aug. 19, 2010.
International Search Report and Written Opinion of related International Application No. PCT/US2009/057253 mailed Nov. 2, 2009.
International Search Report and Written Opinion of related International Application No. PCT/US2009/057264 mailed Nov. 10, 2009.
International Preliminary Report on Patentability of related International Application No. PCT/US2009/057264 mailed Mar. 31, 2011.
International Search Report and Written Opinion of International Application No. PCT/US2009/057372 mailed Nov. 13, 2009.
International Preliminary Report on Patentability of related International Application No. PCT/US09/057382 mailed Mar. 31, 2011.
International Search Report and Written Opinion of International Application No. PCT/US09/057382 mailed Feb. 1, 2010.
International Preliminary Report on Patentability and Written Opinion of related International Application No. PCT/US2009/057372 mailed Mar. 31, 2011.
International Preliminary Report on Patentability Search Report and Written Opinion of related International Application No. PCT/US2009/057253 mailed Mar. 31, 2011.
International Search Report and Written Opinion of International Application No. PCT/US2009/032991 mailed Aug. 6, 2009.
Communication pursuant to Rules 161(2) and 162 EPC of related European Application No. 09815226.7 May 12, 2011.
Communication pursuant to Rules 161(2) and 162 EPC of related European Application No. 09815166.5 May 13, 2011.
Communication pursuant to Rules 161(2) and 162 EPC of related European Application No. 09815223.4 May 12, 2011.
Communication pursuant to Rules 161(2) and 162 EPC of related European Application No. 09815172.3 May 25, 2011.
Extended Search Report of related European Application No. 09815223.4 dated Oct. 2, 2012.
Communication pursuant to Rules 70(2) and 70a(2) EPC of related European Application No. 09815223.4 dated Oct. 19, 2012.
Schackleford et al., CRC Materials Science and Engineering Handbook, 3rd ed., 2000, Table 154.
Extended Search Report of related European Application No. 09815166.5 dated Oct. 22, 2012.
Extended Search Report of related European Application No. 09815226.7 May 9, 2014.
Sengupta, D.K., et al. "Laser Conversion of Electrical Properties for Silicon Carbide Device Applications", Jour. of Laser Applications, vol. 13, Jan. 1, 2011, pp. 26-31.
Wang et al., "Miniaturized Glucose Sensors Based on Electrochemical Codeposition of Rhodium and Glucose Oxidase onto Carbon-Fiber Electrodes," 1992, The American Chemical Society, vol. 64, pp. 456-459.

* cited by examiner

ELECTRICAL DEVICES WITH ENHANCED ELECTROCHEMICAL ACTIVITY AND MANUFACTURING METHODS THEREOF

RELATED APPLICATIONS

The present application claims priority to U.S. Provisional Patent Application No. 61/098,728 filed Sep. 19, 2008, and entitled "ELECTROCHEMICAL DEVICES WITH ENHANCED ELECTROCHEMICAL ACTIVITY AND MANUFACTURING METHODS THEREOF" which is hereby incorporated herein by reference in its entirety for all purposes.

FIELD OF THE INVENTION

The present invention relates to electrochemical apparatus and methods of manufacturing thereof.

BACKGROUND OF THE INVENTION

Devices that include electrochemical activity (sometimes referred to as electrochemical reactivity) find many uses. One use is in the monitoring of an analyte concentration level in a bio-fluid as part of health diagnostics. For example, an electrochemical analyte sensor may be employed for the monitoring of an analyte level (e.g., glucose level) in a patient's blood. Because conventional electrochemical analyte sensors may have relatively low sensitivity, a relatively large bio-fluid sample volume may be required in order to yield an accurate measurement of an analyte concentration level.

Another area of devices where electrochemical activity is of interest is in the area of electrochemical conversion devices (e.g., fuel cells and/or batteries, etc.).

Such conventional electrochemical devices (e.g., analyte sensors, fuel cells, batteries, etc.) may require the use of precious metals and/or may require wet processing steps, which may add significantly to the cost of manufacturing such devices.

Accordingly, it would be beneficial to provide inexpensive electrochemical devices, which may have enhanced properties, such as electrochemical activity.

SUMMARY OF THE INVENTION

In one aspect, the present invention provides a sensor including a sensor member of a semiconductor material, the sensor member including a surface region of enhanced electrochemical activity.

In another aspect, the present invention provides an analyte sensor for detecting an analyte concentration level in a bio-fluid sample. The analyte sensor includes a first sensor member comprised of a semiconductor material; a surface region of enhanced electrochemical activity formed on the sensor member; and an active region positioned in contact with at least a portion of the surface region of enhanced electrochemical activity.

In a method aspect, the present invention provides a method of manufacturing a sensor including the steps of providing a sensor member including a semiconductor material; and providing a surface region of enhanced electrochemical activity on the sensor member.

In another method aspect, the present invention provides a method of manufacturing an electrochemically active device, including the steps of providing a member including a semiconductor material; and applying heat to a surface region of the member to bring about a change in an electrochemical activity of the surface region.

In another aspect, the present invention provides an electrochemical device. The device includes a member of a porous semiconductor material, the member including a surface region of enhanced electrochemical activity.

In yet another aspect, the present invention provides an electrochemical sensor, including a member of a semiconductor material, the member including a region of enhanced conductivity.

Other features and aspects of the present invention will become more fully apparent from the following detailed description, the appended claims, and the accompanying drawings.

DETAILED DESCRIPTION

According to a first aspect of the present invention, an electrochemical device is provided including a member made, at least in part, of a semiconductor material. A surface portion of the member may include a surface region of enhanced electrochemical activity (hereinafter referred to as an "enhanced surface region" or an "enhanced region"). "Surface region of enhanced electrochemical activity" as used herein means a surface region having increased electrochemical reactivity, that is, more rapid oxidation and/or reduction kinetics at a given electrical potential as compared to an untreated surface region of an article of the same size and material.

This region may be formed by the application of heat, i.e., it may be thermally induced. The enhanced surface region may allow for enhanced electrical current generation in electrochemical sensors and devices, such as in analyte sensors and fuel cells, for example. Further, this enhancement may simplify construction by reducing or eliminating a need for precious metals and/or a need for wet processing steps. In some embodiments, the semiconductor material may be silicon carbide. In other embodiments, the member may include a porous semiconducting material (e.g., porous semiconducting foam).

In some embodiments, the device may be an analyte sensor that may include a sensor member made at least in part of a semiconductor material. The sensor member may include a surface region of enhanced electrochemical activity. An active region (e.g., one or more catalytic agents and/or reagents) may be provided in contact with the enhanced region. Accordingly, the sensor may be used for analyte detection. In operation, the active region may be adapted to react with, and convert, an analyte in a bio-fluid sample into reaction products from which an electrical current may be generated.

The sensor member may be disposed in another element, such as a base or hollow member (e.g., a needle-like member) wherein the sensor may operate as a working electrode of the sensor, for example. Advantageously, providing a surface region of enhanced electrochemical activity on the sensor may provide enhanced signal generation as compared to like articles without the enhanced activity surface.

These and other embodiments of electrochemical devices, sensors, analyte sensors, apparatus including the analyte sensors, and methods for manufacturing the devices and sensors are described below with reference to FIGS. 1-14.

Figure 1:
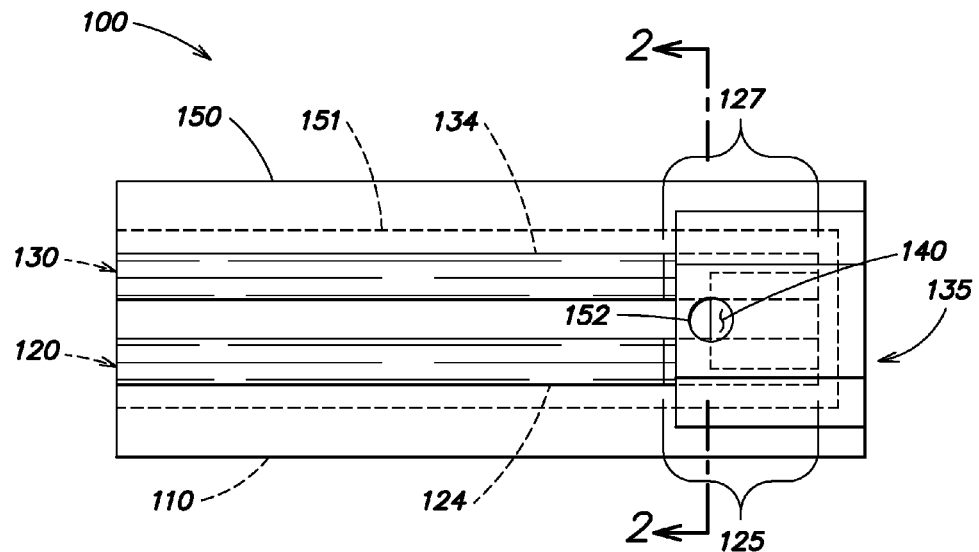
FIG. 1 is a top plan view of an exemplary embodiment of an analyte sensor provided according to the present invention.
Figure 2:
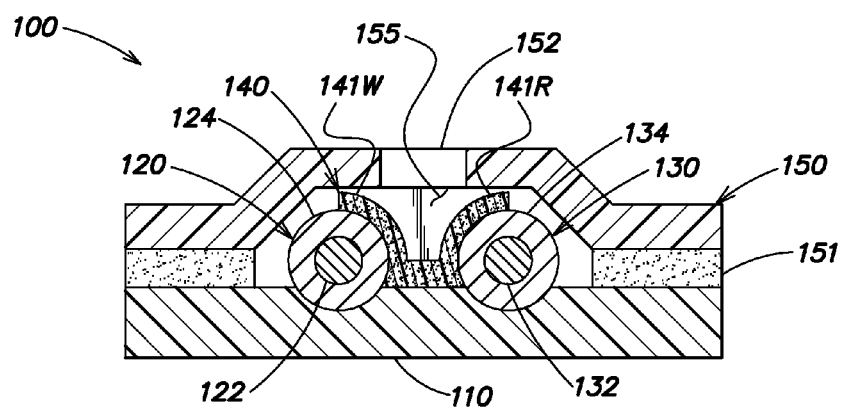
FIG. 2 is an enlarged cross-sectional view of an analyte sensor of FIG. 1 taken along section line 2-2.
Figure 3:
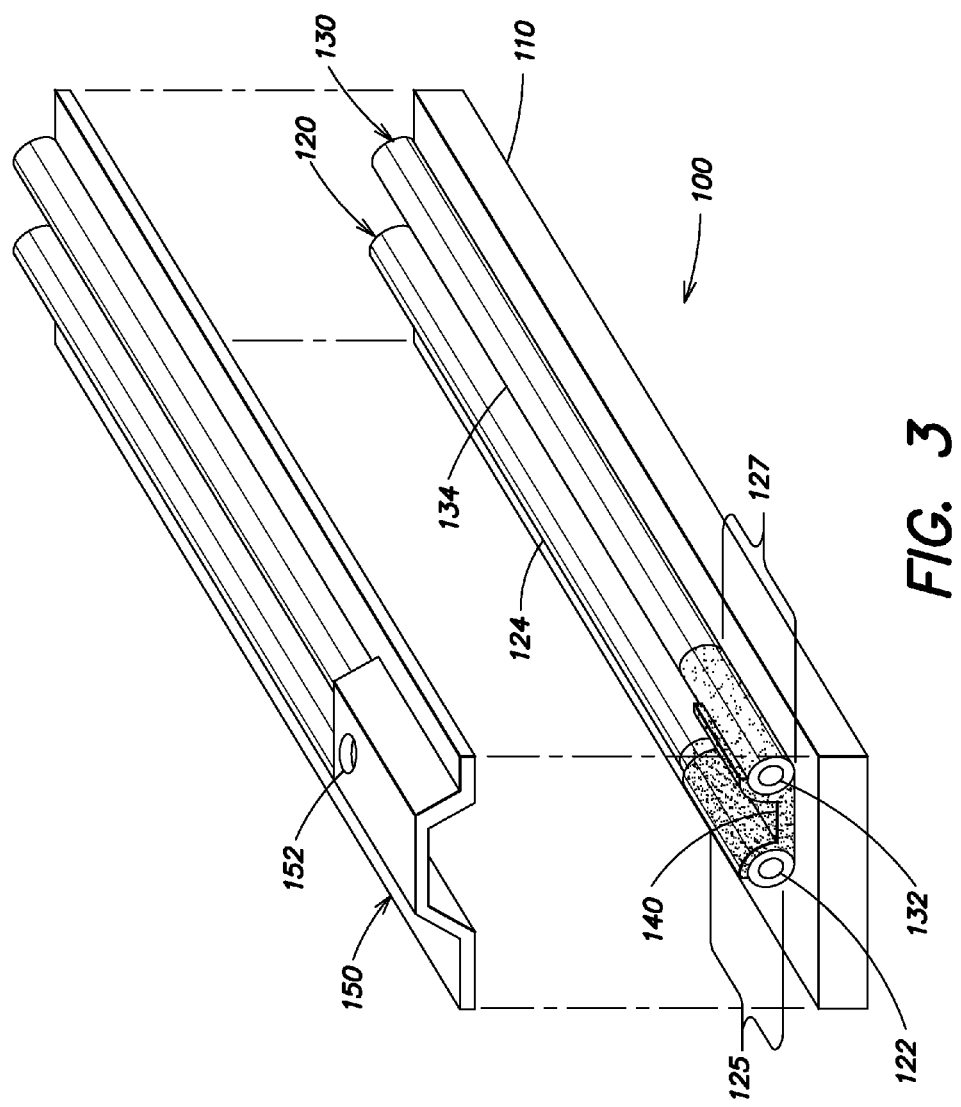
FIG. 3 is an exploded isometric view of the exemplary embodiment of an analyte sensor of FIG. 1 according to the present invention showing a lid being separated for clarity.

FIGS. 1-3 show various views of an exemplary embodiment of an analyte sensor 100 provided according to the present invention. The analyte sensor 100 may include a base 110 which may be formed of any suitable insulating material such as a polymer (e.g., polycarbonate, polystyrene, high density polyethylene, polyethylene terephthalate, polyimide, or like insulating material). The base 110 may have a first sensor member 120 mounted thereon, which may be mounted by including some level of physical impression into the base 110. For example, when the base 110 is a deformable polymer sufficient pressure and/or heat may be applied thereby causing a cladding 124 of first sensor member 120 to impress into the base 110. Furthermore, the impression may be molded into the base 110. Optionally, the first sensor member 120 may be adhered or glued, heat fused, ultrasonically fused, or otherwise mounted to the base 110. In some embodiments, the first sensor member 120 may be mounted to the base 110 simply by sandwiching between the base 110 and a lid 150. An adhesive 151 may be used to attach the lid 150 to the base. The base 110 may be of any suitable size and shape.

In some embodiments, the first sensor member 120 may include a core 122 made of a conductive material, and the cladding 124 which may be made at least in part of a semiconductor material. In some embodiments, the first member 120 may take the form of a fiber including a semiconductor material, and in some embodiments the conducting core 122 may be at least partially surrounded by a semiconducting cladding 124. The fiber may have a circular cross section and include a length substantially longer than a transverse dimension (e.g. diameter) thereof.

In the exemplary embodiment shown, the cladding 124 may include an annular shape and may fully surround the core 122 along at least a portion of a length of the core 122. The core 122 may have a shape of a cylindrical rod, for example. Both the core 122 and the cladding 124 may convey, in operation, electrical current. In some embodiments, the core 122 may comprise carbon (e.g. graphite) and the cladding 124 may comprise silicon carbide (SiC). Silicon carbide/carbon fibers having a suitable SiC cladding and carbon core are manufactured by Specialty Materials Inc. of Lowell, Mass., for example. However, the conductive material of the core 122 may also comprise other electrically-conductive materials including metals such as the noble metals, copper, aluminum, etc. The cladding 124 may comprise other semiconductor materials including Group IV elements such as silicon and germanium, Group IV compounds such as silicon germanide (SiGe), and Group III-V compounds such as gallium arsenide (GaAs) and indium phosphide (InP), among others.

In some embodiments, the first sensor member 120 may have a total diameter (including the core 122 and cladding 124) of about 150 microns or less, about 100 microns or less, about 75 microns or less, or even about 50 microns or less. In some embodiments, the diameter of the first sensor member 120 may range between about 75 microns and about 150 microns (although larger or smaller sizes may also be used). The core 122 may have a diameter between about 10 microns to about 100 microns, or even between about 20 microns to about 40 microns, and may be about 30 microns in some embodiments. Other dimensions may also be used.

In the depicted embodiment, the first sensor member 120 may include an end portion with a region of thermally-induced, enhanced electrochemical activity 125 (the "enhanced region"). The formation of this region 125 is described below more thoroughly. As is illustrated by the plot in FIGS. 11A and 11B, an analyte sensor including the enhanced area on a SiC cladding may increase the response to the analyte (e.g., glucose) by greater than about five times, or even greater than about 10 times, for example. Accordingly, a substantially greater response to the analyte is provided by this aspect of the present invention as compared to a like SiC member without the enhanced region. In some embodiments described herein, a current density upon exposure of the sensor to an analyte is greater than 1 $\mu A/cm^2$, or even greater than 10 $\mu A/cm^2$.

The analyte sensor 100 may further include a second sensor member 130, which in a preferred implementation includes a core 132, which may be manufactured from a conductive material, and a cladding 134, which may include a semiconductor material. The materials for the second sensor member 130 may be the same as described above for the first sensor member 120. Optionally, the second sensor member 130 may be made of more conventional materials, such as carbon, graphite, gold, silver, palladium, platinum, etc. For example, the second sensor may be formed of a carbon/graphite PTF. It should be recognized that the reference electrode may take on other forms (e.g., a coil, foil, strip, or film).

In some embodiments, however, the second sensor member 130 may be, as shown in FIG. 1, another fiber, which may be oriented in a generally parallel relationship to the first sensor member 120. Other orientations may be provided, such as nonparallel. If the second sensor 130 includes a semiconductor cladding (e.g., SiC), then the sensor member 130 may include a region of thermally-induced, enhanced electrochemical activity 127, as described above for the first sensor member 120. The second sensor member 130 may function as a reference electrode providing a return path for an electrical current. In one or more embodiments, the second sensor member 130 may function as a counter electrode.

Again referring to FIGS. 1-3, applied onto the base 110 and in contact with, and electrically coupled to, at least the first member 120 is an active region 140, described below more thoroughly. Briefly, however, the active region 140 may be adapted to be exposed to the bio-fluid sample, and may include one or more catalytic agents or reagents adapted to promote an electrochemical reaction between an analyte in the bio-fluid sample and the catalytic agents or reagents included in the active region 140. This may produce reaction products and mobile electrons, which then may be conducted, for example, by the core 122 or cladding of the first sensor member 120. A mediator, to be described later herein, may also be provided in the active region 140 to aid in carrying the electrons to the surface of the core 122 or cladding 124.

According to embodiments of the invention, a cavity 155 may be formed and provided proximate to an open end 135 of the first sensor member 120. The cavity 155 (FIG. 2) may receive a bio-fluid sample inserted in the open end 135 of the sensor 100, for example. In particular, the cavity 155 may be at least partially formed and defined, for example, by inner surfaces of the lid 150 and surfaces of the base 110 (with active region 140 applied thereto). The cavity 155 may have any shape, but preferably has a shape, which promotes capillary action to cause a droplet of bio-fluid to be drawn in and come to rest between the respective regions 125, 127 such that the sample is provided in contact with the active region 140. A hole 152 may be provided to assist in release of displaced air and to promote capillary action.

In some embodiments, a sufficient bio-fluid sample for purposes of detecting an analyte concentration level may have a volume of less than about 0.5 microliters, less than about 0.4 microliters, or even less than about 0.3 microliters, for example. Some exemplary embodiments may require a sample volume to detect an analyte concentration level of less than about 0.2 microliters, less than about 0.1 microliters, or even less than about 0.05 microliters, for example. Other sample volumes may also be employed.

Contributing to the need for a lessened volume of the bio-fluid sample may be the use of the fiber-like shape of the first sensor member 120. This is thought to provide generally-opposed surfaces 141W, 141R (wherein "W" stands for "Working" and "R" stands for "Reference") for the active region 140, thus providing a three-dimensional shape, as well as a relatively large effective surface area of exposed electrode. As such, excellent analyte detection may be accomplished with a relatively small sample size of the bio-fluid. Moreover, because of the addition of an enhanced region, a substantially higher signal level may be provided (See FIG. 11). Accordingly, a propensity to have to prick the finger, etc., a second time to obtain sufficient fluid volume for testing may be minimized or avoided.

Figure 4:
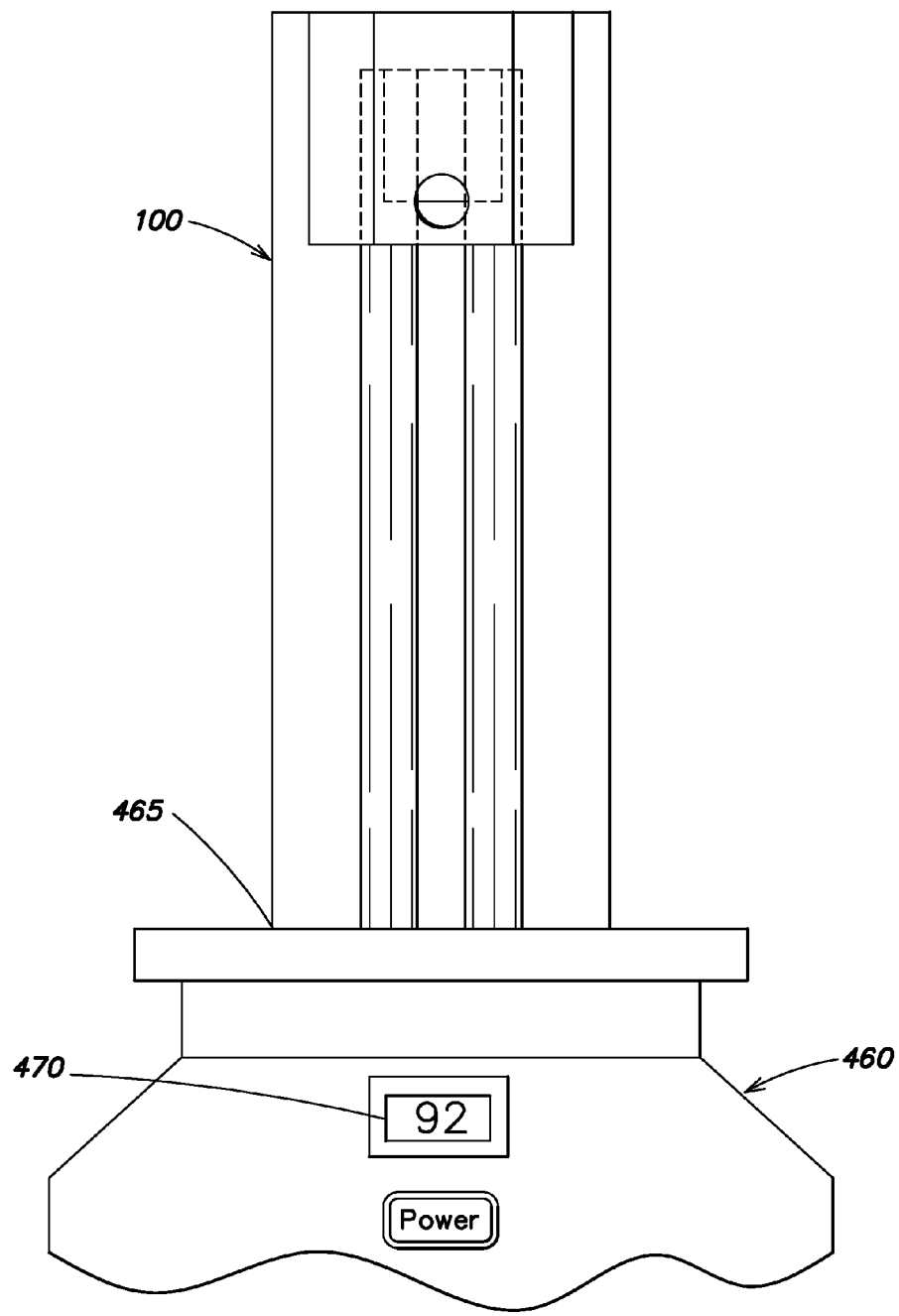
FIG. 4 is a partial frontal view of a testing apparatus receiving an exemplary embodiment of an analyte sensor according to the present invention.

Referring to FIG. 2, the active region 140 may be positioned within the cavity 155, and is preferably located at a bottom of the cavity 155, thereby allowing exposure of the active region 140 to the sample bio-fluid that enters the cavity 155. As shown, the active region 140 is applied over, and in contact with, the claddings 124, 134. In particular, the active region 140 may be applied over at least a portion of a length of the enhanced regions 125, 127. Upon insertion of the bio-fluid sample into the cavity 155, the cladding 124 and/or core 122 may then conduct and channel electron flow and provide an electrical current, which may be proportional to the concentration of the analyte in the bio-fluid sample. This current may then be conditioned and displayed on a testing apparatus 460 including any suitable readout, such as a digital readout 470 (such as shown in FIG. 4).

As further shown in FIG. 4, an embodiment of an analyte sensor 100 such as the analyte sensor described with reference to FIGS. 1-3, or any of the additional embodiments described herein, may be inserted and received into a port 465 of the testing apparatus 460. Electrical contacts (not shown) in the apparatus 460 come into electrical contact with conductive ends of sensor members 120, 130 (e.g., the cores and/or cladding thereof) thereby making an electrical connection to the circuitry of the apparatus 460. Upon applying a voltage bias (e.g., about 400 mV), conventional processing programs and circuitry may then equate the current supplied by the sensor 100 to an analyte concentration level.

Again referring to FIGS. 1-3, one group of catalytic agents useful for providing the active region 140 is the class of oxidase enzymes which includes, for example, glucose oxidase (which converts glucose), lactate oxidase (which converts lactate), and D-aspartate oxidase (which converts D-aspartate and D-glutamate). In embodiments in which glucose is the analyte of interest, glucose dehydrogenase (GDH) may optionally be used. Pyrolloquinoline quinine (PQQ) or flavin adenine dinucleotide (FAD) dependent may also be used. A more detailed list of oxidase enzymes which may be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes may also be used.

The active region 140 may include one or more layers (not explicitly shown) in which the catalytic agents (e.g., oxidase enzymes) and/or other reagents may be immobilized or deposited. The one or more layers may comprise various polymers, for example, including silicone-based or organic polymers such as polyvinylpyrrolidone, polyvinyl alcohol, polyethylene oxide, cellulosic polymers such as hydroxyethylcellulose or carboxymethyl cellulose, polyethylenes, polyurethanes, polypropylenes, polyterafluoroethylenes, block co-polymers, sol-gels, etc. A number of different techniques may be used to immobilize the enzymes in the one or more layers in the active region 140 including, but not limited to, coupling the enzymes to the lattice of a polymer matrix such as a sol gel, cross-linking the agents to a suitable matrix such as glutaraldehyde, electropolymerization, and formation of an array between the enzymes via covalent binding, or the like.

In some embodiments, an electrochemically-active layer (not explicitly shown) may be positioned adjacent to a working end 135 of the core 122 or cladding 124. The electrochemically-active layer may include, for example, deposited metals, such as a noble metal such as platinum, palladium, gold or rhodium, or other suitable materials. In a glucose detection embodiment, the active layer may undergo a redox reaction with hydrogen peroxide when polarized appropriately. The redox reaction causes an electrical current to be generated by electron transfer that is proportional to the concentration of the analyte that has been converted into hydrogen peroxide. This current may be conducted and conveyed from the electrochemically-active layer through the core 122 and/or cladding 124 to a testing apparatus 460 as previously described with reference to FIG. 4.

In some embodiments, a mediator may be within the active region 140 to promote the conversion of the analyte to detectable reaction products. Mediators comprise substances that act as intermediaries between the catalytic agent and the working electrode (e.g., the surface of the core, cladding, an electrochemically active layer applied to the core, or the enhanced region etc.). For example, a mediator may promote electron transfer between the reaction center where catalytic breakdown of an analyte takes place and the working electrode, and may enhance electrochemical activity at the working electrode. Suitable mediators may include one or more of the following: metal complexes including ferrocene and its derivatives, ferrocyanide, phenothiazine derivatives, osmium complexes, quinines, phthalocyanines, organic dyes as well as other substances. In some embodiments, the mediators may be cross-linked along with catalytic agents directly to the working electrode.

To form an electrochemical cell, the second sensor member 130 may be coupled to the active region 140 in the cavity 155. In particular, the active region 140 may be applied to be in contact with and configured to extend between the claddings 124, 134 having the enhanced regions 125, 127 formed thereon. The active region 140 may extend along the generally-opposed surfaces 141W, 141R of the claddings 124, 134 as best shown in FIG. 2, such that a drop of bio-fluid may be received in a three-dimensional feature formed by the active region 140 as applied over the surfaces of the claddings 124, 134 and base 110.

Figure 5:
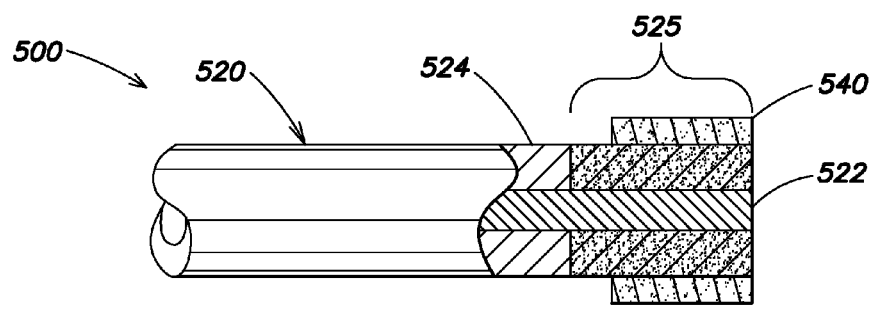
FIG. 5 is a partially cross-sectioned top plan view of another exemplary embodiment of an analyte sensor according to the present invention.

FIG. 5 is a partially cross-sectioned, partial view of another embodiment of an analyte sensor 500 according to the present invention. The sensor 500 comprises a sensor member 520 comprising a semiconductor material. The sensor 500 may include a rod-like core 522 of a conductive material, and may include a cladding 524 formed at least in part of a semiconductor material. In some embodiments, the member 520 may be provided in the form of a fiber with the cladding 524 surrounding and encircling the core 522 along at least a portion of the length of the fiber. In this embodiment, the cladding 524 includes a region of thermally-induced, enhanced electrochemical activity 525.

An active region 540 may be included in contact with at least a portion of the enhanced region 525 of the sensor member 520. The active region may be the same as described above. The active region 540 applied to the region of thermally-induced, enhanced electrochemical activity 525 may enhance the electrochemical activity and analyte response as will be described below in more detail. The analyte sensor 500 may be included within another structure or device, such as within a cavity or within a hollow member.

Figure 6:
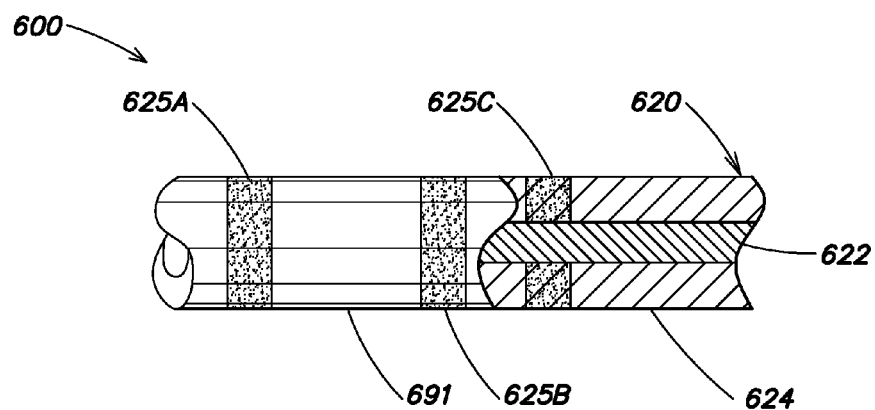
FIG. 6 is an enlarged, partially cross-sectioned top plan view of a coded region of an embodiment of an analyte sensor according to the present invention.

Additionally, in the depicted embodiment of FIG. 6, a sensor member 620 of an analyte sensor 600 may be provided with an annulus or annuli, which constitute one or more regions of thermally-induced, altered conductivity 625A-625C. In particular, the enhanced regions 625A-625C may provide for the application of information coding, for example. The coding may allow certain information to be coded onto the sensor member 620. The coded information may relate to the properties and/or features of the sensor 600, for example. In particular, a date of manufacture, lot number, part number or version number, calibration data or constants, expiration date, or the like may be encoded. This coded information may be read by the testing apparatus (e.g., apparatus 460 shown in FIG. 4) upon insertion of the sensor 600 in the apparatus.

As best shown in enlarged view in FIG. 6, and in the case where a semiconductor cladding material is used (e.g., SiC), the regions of thermally-induced, altered conductivity 625A-625C may be formed of, and include, one or more altered conductivity tracks (e.g., rings). The tracks may be formed on the cladding 624 of the sensor member 620, and may extend inwardly in a radial direction to the core 622. In the depicted embodiment, three altered conductivity tracks 625A-625C are shown. However a greater or lesser number of tracks may be used. For example, in one embodiment, a single track of variable width may be used, wherein a two-point measurement of resistance may be taken to measure and determine a level of resistance. That resistance value may then be correlated to a code in a look-up table, for example. The resistance level may be varied by adjusting the power and/or sweep conditions employed when forming the track, for example.

In the depicted embodiment of FIG. 6, the plurality of spaced, altered conductivity tracks may be provided on the sensor member 620. The tracks positioned on the member 620 may be used to provide bits of coded information (e.g., 1's and 0's) which thereafter may be read from the member 620 by a suitable reader provided in a testing apparatus (See FIG. 4)). For example, a track existing at a defined location spaced from a terminal end of the sensor 600 may be used to signify a "1," while the absence of a track at a defined location (see location 691) may indicate a "0." Accordingly, with only 4 predetermined track locations, $2^4$ bits or 16 codes may be provided which then may be read by a testing apparatus (not shown), for example. The testing apparatus may include electrical contacts (not shown) which contact at each spaced location where a track may be placed, and may read out a resistance value to determine the bits (1 or 0) at each location. In some embodiments, it may be desirable to code information on other sensor members, if provided.

Figure 7:
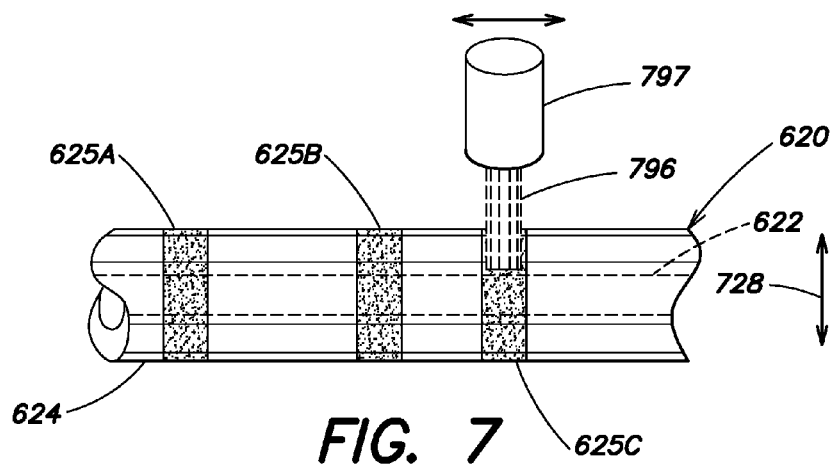
FIG. 7 is a partial top plan view illustrating a formation of tracks on a sensor member included within an exemplary embodiment of an analyte sensor according to the present invention.

As best shown in FIG. 7, a method of forming one or more regions of thermally-induced, altered conductivity 625A-625C is provided. Each of the regions 625A-625C may be formed, for example, by subjecting the SiC cladding 624 of the sensor member 620 to intense localized heat at a suitable temperature. The surface temperature provided should be sufficient to provide a suitable alteration in the conductivity of a region relative to the nonprocessed regions. In the case of formation of the enhanced activity region, a suitable temperature may be employed to provide a suitable alteration in electrochemical activity relative to the nonprocessed regions. A suitable surface temperature for formation of the regions may be greater than about 1,000° C., greater than about 1,500° C., or even greater than about 2,000° C., for example.

For example, the cladding 624 may be exposed to a laser beam 796 emitted from a laser 797 as the member 620 or laser 797 are subjected to perpendicular motion relative to the other (designated by arrow 728). The fiber may then be rotated or flipped over 180 degrees and the same process repeated on the other side. In some cases, it may be more efficient to process many fibers in a side by side orientation subjecting them all to a common laser treatment.

The laser 797 may be any suitable laser, having suitable power to effectuate an appropriate thermal change in the fiber. One suitable laser may be a yttrium vanadate laser ("Y-VO$_4$ laser") having a power of between about 5 and 250 watts and providing a beam width of between about 30 microns and about 250 microns, for example. The wavelengths used can be the natural wavelength of about 1064 nm, the frequency doubled wavelength (about 532 nm) or frequency tripled wavelength (about 355 nm). The scanning movement of the member 620 may be such that a surface rate of the laser beam 796 in the perpendicular direction may be at a scan rate of between about 20 mm/s and 2000 mm/s, and in some embodiments about 200 mm/s. In the case where large areas of the members are being treated, the laser 797 may scan in the Y direction and then be spaced incrementally along a longitudinal length (X direction) of the member 620 by a small increment and the scan repeated in the Y direction. The increment may be small enough such that the affected regions abut or overlap slightly. The laser may scan a plurality of parallel aligned fibers at once, in both X and Y directions, that is the scan may cover a square or rectangular field and marks the entire desired pattern without moving the fibers. The fibers may be flipped over to treat the previously hidden underside. This sequence of scanning and spacing may be repeated until a region of the desire length is formed. The laser may be pulsed at a frequency of between about 10 kHz and about 100 KHz. Other high-powered lasers may be used, such as YAG, $CO_2$, excimer, laser diodes, slab, thin disc, fiber, and green lasers.

The intense localized heating of the cladding 624 comprised of semiconductor material (e.g., SiC) may cause a localized alteration in resistivity and/or electrochemical activity of the cladding 624. As such, the localized heating may provide an altered conductivity track or tracks 625A-625C encircling the core 622 (shown dotted). In some embodiments, the region may penetrate radially into the member to a depth sufficient to reach the core 622. Upon exposure to sufficient heat, the tracks 625A-625C may have a conductivity, which may be several orders of magnitude, or more different from a surrounding SiC material not subjected to the heat from the laser application. Further, in the case where an enhanced region is formed, such as in the embodiments of FIG. 1-3, FIGS. 5, 8A-8D, and 14, for example, the method described above may be used.

In accordance with another aspect, a fill detector function may be provided proximate to the active region to ensure that a sufficient bio-fluid sample is present when performing a detection of an analyte concentration. For example, a fill detector function may be provided by producing a conductive track (like track 625C) on each of two sensor members (a first sensor member and a second sensor member) at a position proximate the active region. For example, the fill detector track may be provided an equal distance from the active region on each sensor member. The tracks may be formed as described above.

In operation, if a sufficient bio-fluid sample is present, a portion of a bio-fluid sample will come to rest between the fill detector tracks formed on the sensor members and provide a conductive path through the bio-fluid sample. Accordingly, when the bio-fluid is present at the location of the fill detector tracks, then a significant lowering of electrical resistance between the sensor members may be measured.

Figure 8A:
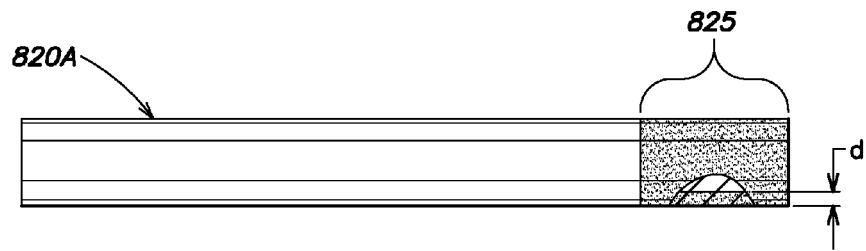
FIGS. 8A-8D are top plan views of other exemplary embodiments of sensor members for inclusion in analyte sensors according to the present invention.
Figure 8B:
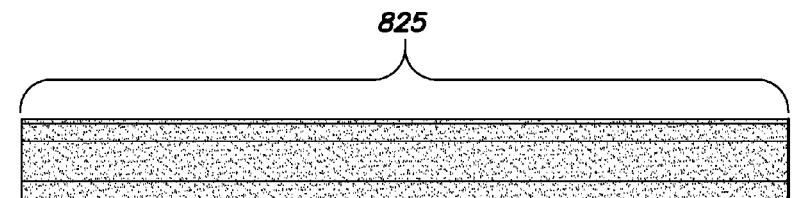
Figure 8C:
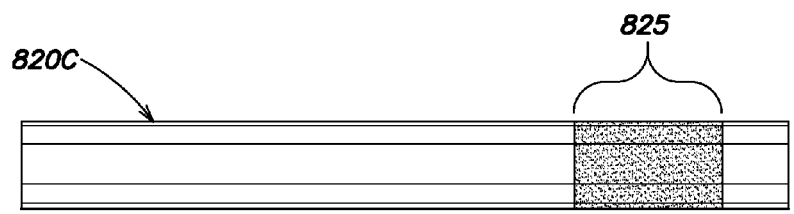
Figure 8D:
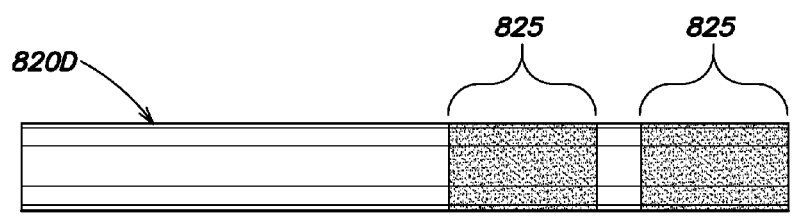

FIGS. 8A-8D illustrate various embodiments of sensor members 820A-820D, respectively, according to the present invention. In the first embodiment of FIG. 8A, the sensor member 820A may be formed as a fiber including a semiconductor material (e.g., a cladding of SiC) and may include a region of enhanced electrochemical activity 825 only on an end portion of the semiconducting member 820A. This region 825 may be formed on a surface region of a semiconducting portion of the semiconducting member, and may be thermally induced as described above, for example. Optionally, the enhanced region 825 may be formed elsewhere on the member, such as in the middle (FIG. 8C), or at several longitudinally-spaced locations (FIG. 8D). In these embodiments, the enhanced region 825 may be provided on less than all of a peripheral radial surface of the member 820C, 820D, respectively. The region(s) 825 may be provided as an annulus or a plurality of annuli, for example. An active region, such as region 540, as described in the FIG. 5 embodiment, may be applied to at least a portion of the enhanced regions 825 to form an analyte sensor in each case.

In the FIG. 8B embodiment, an entire radial peripheral surface of the member 820B may be provided with a surface region enhanced electrochemical activity 825. In the depicted embodiments, heat (e.g., via a laser beam) may be applied such that the region 825 may be thermally induced on an outer surface of the sensor member 820A-820D. The region 825 may include a radial depth (d), measured from a surface (e.g., a radial peripheral surface) inwardly, of at least 5 microns (see FIG. 8A). In some embodiments, the depth (d) of the region 825 may be at least 10 microns, or even at least 20 microns. In some embodiments, the region 825 may extend to a conductive core of the member 820A-820D.

Figure 9A:
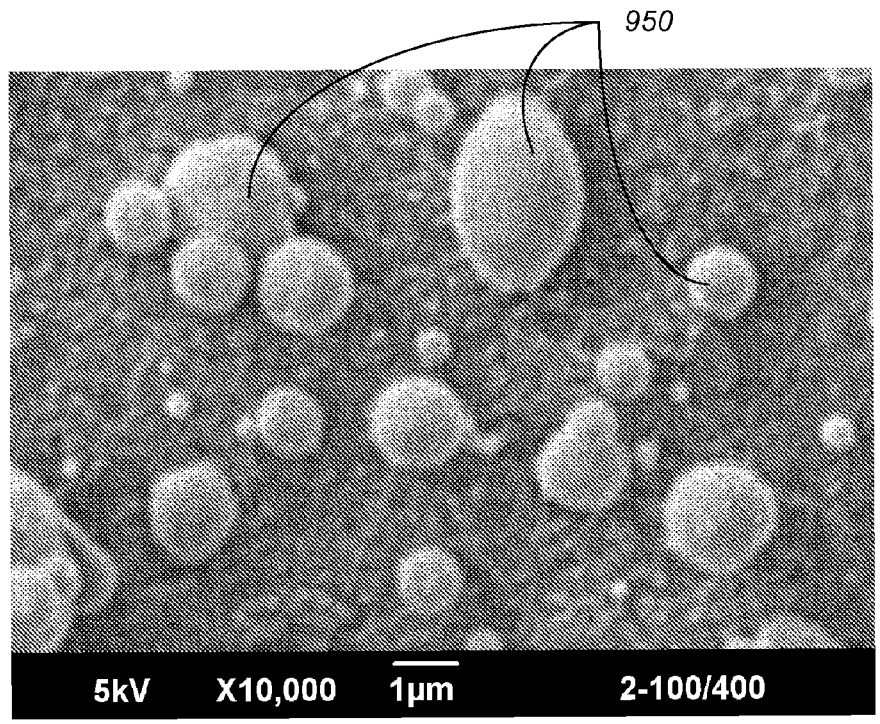
FIG. 9A is a micrograph view at 10,000× magnification of an enhanced electrochemical activity surface according to the present invention.
Figure 9B:
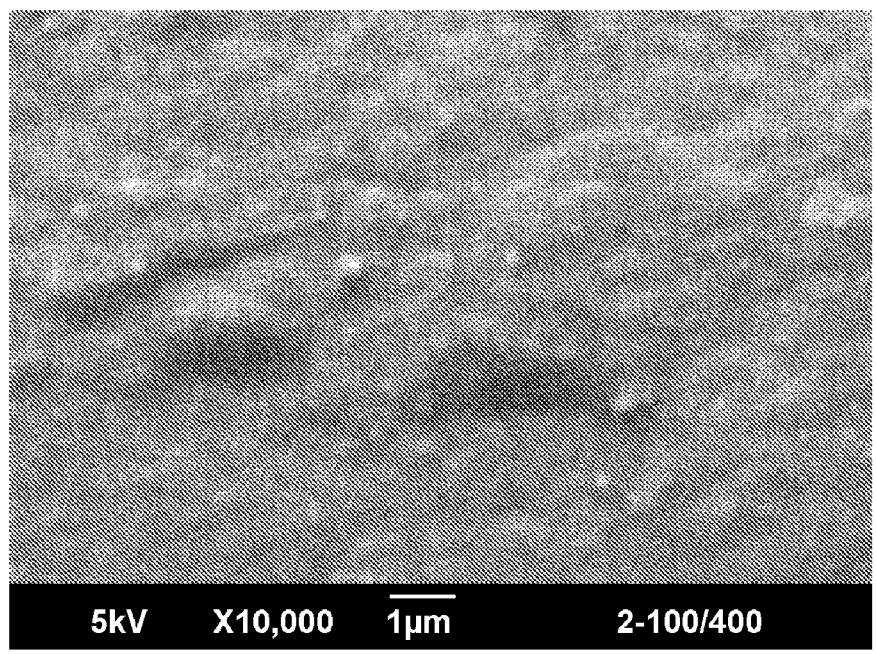
FIG. 9B is a micrograph view at 10,000× magnification of an unenhanced surface for comparative purposes.
Figure 9C:
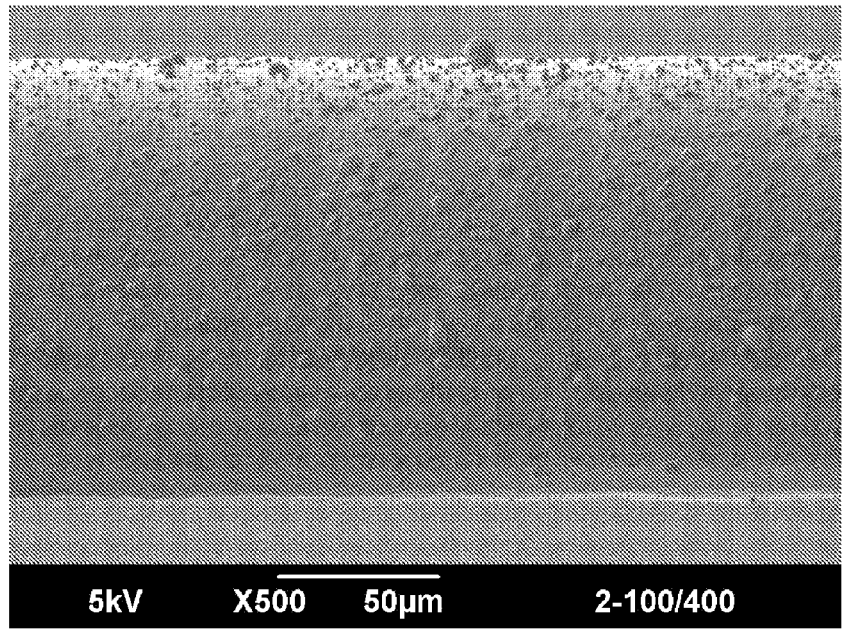
FIG. 9C is a micrograph view at 500× magnification of an enhanced electrochemical activity surface according to the present invention.
Figure 9D:
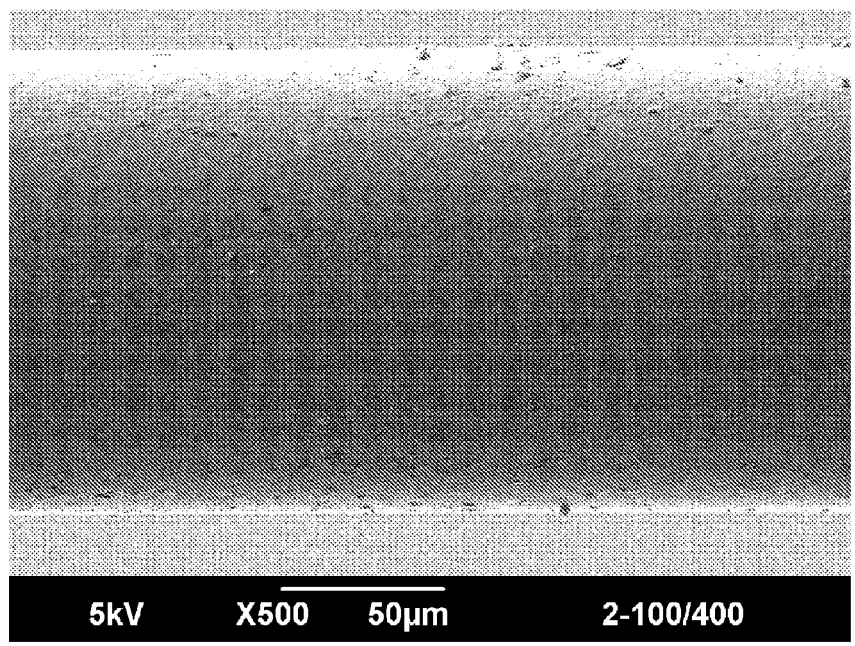
FIG. 9D is a micrograph view at 500× magnification of an unenhanced surface for comparative purposes.

FIGS. 9A-9D illustrate micrographs at various magnifications, with and without a region of thermally-induced, enhanced electrochemical activity 825B provided on a surface of the member. In particular, FIGS. 9A and 9B illustrate surface regions of a semiconducting member (e.g., a semiconducting fiber) at 10,000× magnification, with and without, respectively, a thermal surface treatment (e.g., heating with a laser) providing an enhanced region. FIG. 9A illustrates clearly a change in surface morphology wherein generally spherically-shaped globules 950 are formed on the surface. The globules 950 may vary in cross-sectional maximum dimension from about 100 nanometers to about 5 microns, for example. It is believed that the globules may increase the effective surface area or the effective surface conductivity, or both. In any event, it has been discovered that applying heat to a surface region of the semiconducting member may bring about a change in an electrochemical activity of at least the surface region. FIG. 9B illustrates a like-sized region of the member as compared to the region of FIG. 9A without the application of heat to the surface (an unenhanced region). FIGS. 9C and 9D illustrate further micrographs at 500× magnification illustrating a thermally-induced, enhanced activity surface in FIG. 9C as compared to an unenhanced surface of FIG. 9D at the same magnification.

Figure 10:
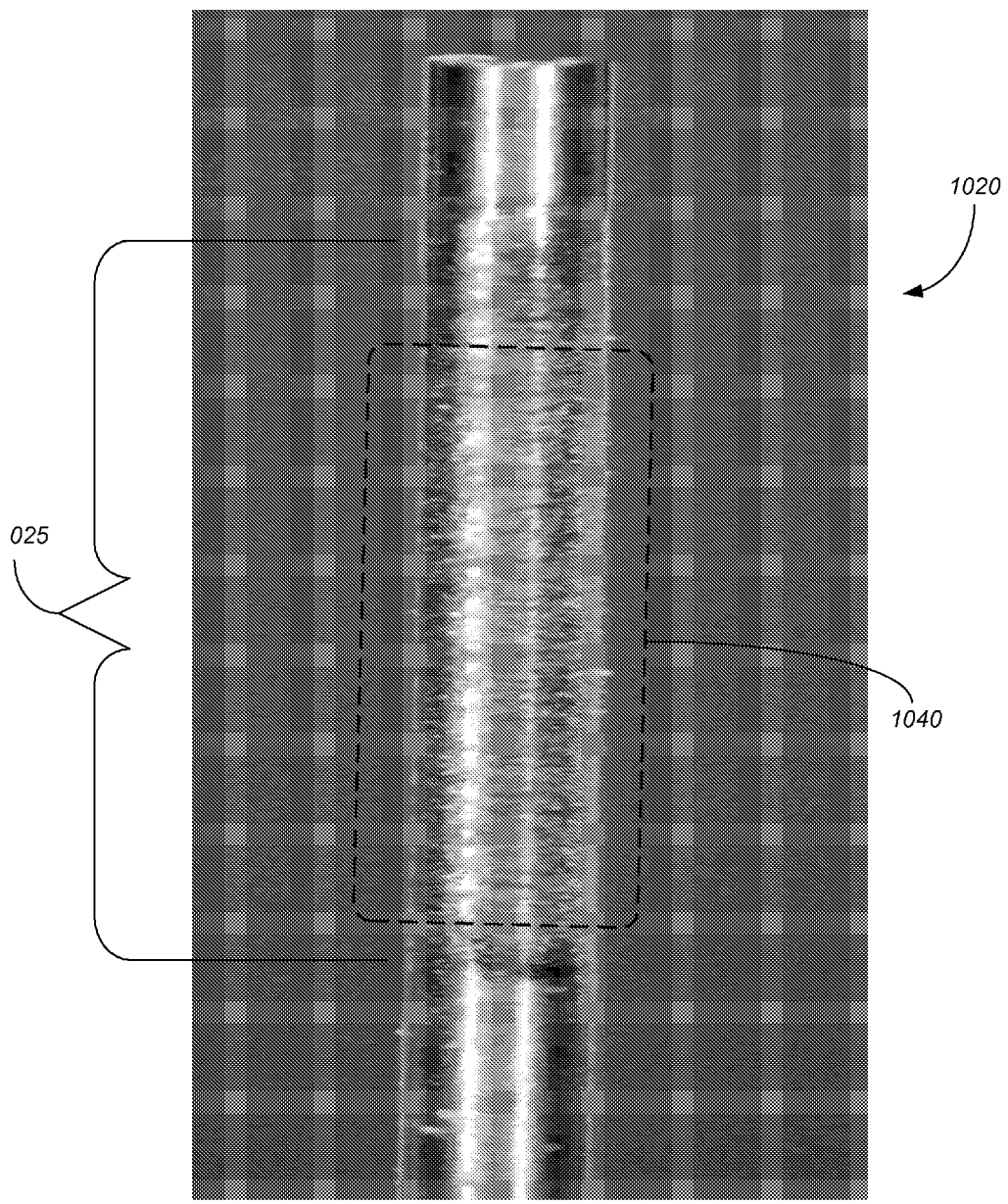
FIG. 10 is a micrograph view of a semiconducting fiber including a surface region of enhanced electrochemical activity surface according to the present invention.

FIG. 10 illustrates an embodiment of a member 1020, which may be a semiconducting fiber and wherein a surface of the semiconducting cladding of the fiber has formed thereon a surface region of enhanced electrochemical activity 1025, which may be thermally induced. As shown, the enhanced region 1025 may be provided on less than all of a surface of the sensor member 1020. As described before, an active region 1040 may be applied to at least a portion of the enhanced region 1025 thereby forming an analyte sensor.

Figure 11A:
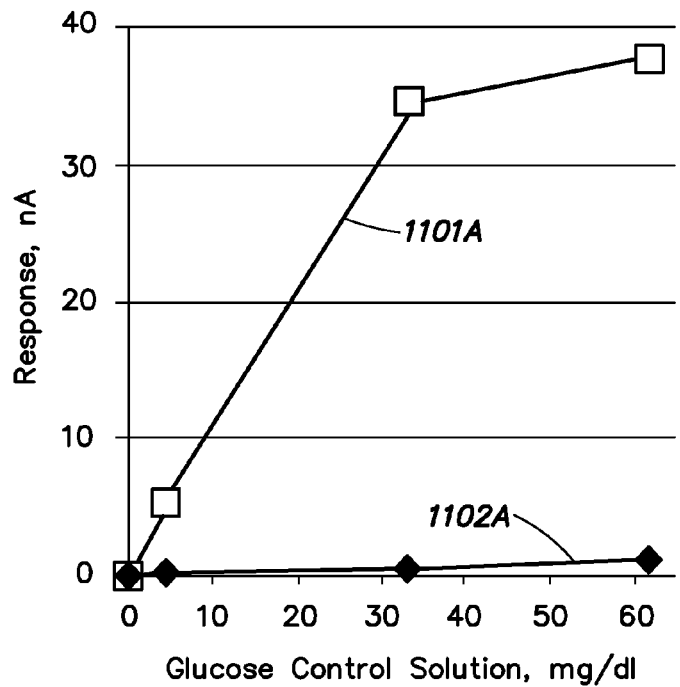
FIG. 11A is a first plot illustrating an electrochemical response (in nA) of an inventive analyte sensor employing a surface region of enhanced electrochemical activity according to the present invention as compared to a comparative analyte sensor without an enhanced surface region.

FIG. 11A illustrates a plot of a electrical response (in nanoamperes (nA)) of a sensor member including a region of enhanced electrochemical activity of the present invention (labeled 1101A) as against a sensor member having no enhanced region (labeled 1102A) upon exposure to various levels of glucose analyte containing control solution. The sensor members were each fibers having an outer silicon carbide cladding of an outer diameter of about 140 microns and a carbon core having a diameter of about 30 microns. The sensor member including an enhanced region was subjected to heating from a YAG laser set at a power of about 50 watts and pulsed at about 100 kHz. The laser beam width was about 65 microns and the fibers were ablated by scanning the laser numerous times across the surface of the fibers at a scan rate of about 200 mm/s and a suitable spacing. Numerous fibers were laid side by side on a flat surface of an anodized backing plate and the laser scan was performed across the width of the collection of fibers. The laser was then spaced along the longitudinal length of the fibers by a small increment (about 0.025 mm) and the scan repeated to produce an exposed region about s 5 mm long. The fibers were then flipped over and the process repeated. The application of heat by the laser provided a region of enhanced electrochemical activity, which was thermally induced. The other sensor member was left untreated (unenhanced).

Each member then had applied thereto a same active region made of 0.9 g ferricyanide, 0.3 g HEC and 0.3 g GOx in a 14.4 g of a 7.4 pH buffer solution by dipping. In the treated fiber, the active region was applied on top of the region of enhanced electrochemical activity. The core of the fibers in this test were sealed to evaluate the effect of the semiconductor cladding. In the test, each sensor member was subjected to an analyte solution containing various concentrations of a glucose control solution from about 4 to about 62 mg/dL. As is demonstrated from the plot, an electrochemical response of the sensor member having an enhanced activity region was greater than about 5 times, or even greater than about 10 times for a 60 mg/dL concentration of glucose solution. Accordingly, analyte sensors including the electrochemically enhanced region of the invention may have a substantially increased electrochemical response (current density) to an analyte (e.g., glucose) as compared to a like untreated fiber.

Figure 11B:
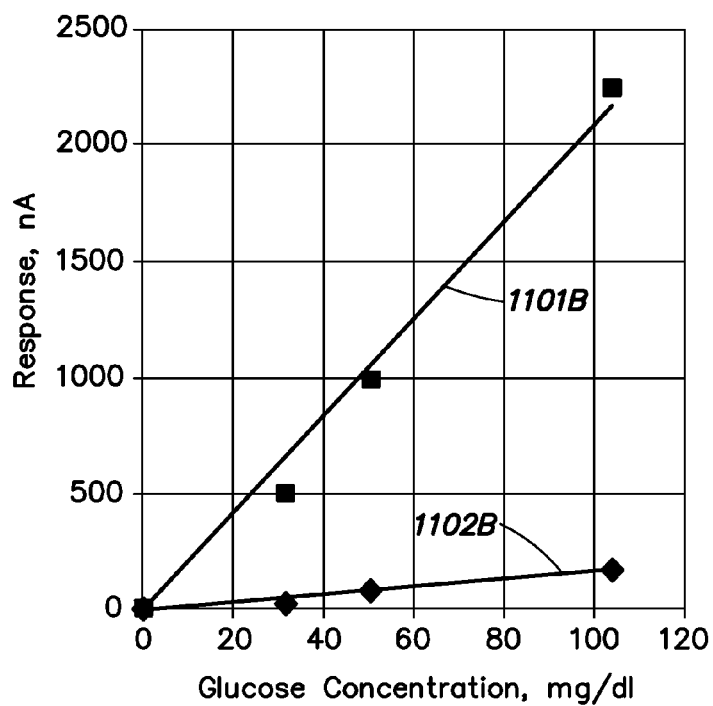
FIG. 11B is a second plot illustrating an electrochemical response (in nA) of an inventive analyte sensor employing a surface region of enhanced electrochemical activity according to the present invention as compared to a comparative analyte sensor without an enhanced surface region.

FIG. 11B demonstrates another comparison of untreated and treated fibers as described above with reference to FIG. 11A, however, in this test, the carbon core was left unsealed in each fiber. The same preparation conditions were used as in the FIG. 11A test, except for the cores being left unsealed. In this test, the treated fiber 1101B having a region of enhanced electrochemical activity formed by laser treatment also shows an increase in response of greater than about 5 times, or even greater than about 10 times as compared to the unprocessed fiber 1102B. These tests may indicate that the enhancement is coming from the heat treatment received by of the SiC cladding of the fiber.

Figure 12:
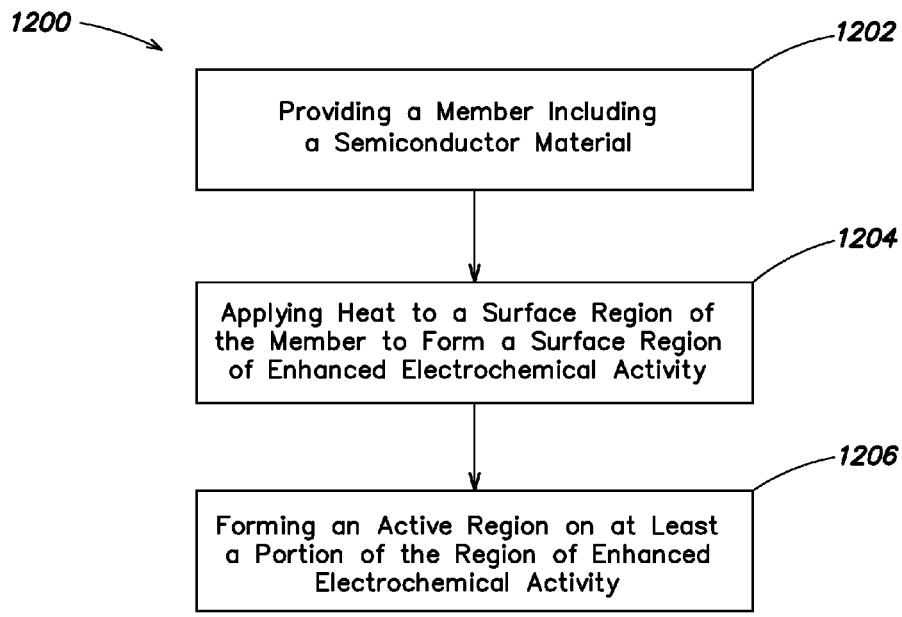
FIG. 12 is a flowchart illustrating methods of manufacturing members including a surface region of enhanced electrochemical activity surface according to the present invention.

A method for manufacturing embodiments of devices with regions of enhanced electrochemical activity surfaces according to aspects of the invention will now be described with reference to FIG. 12. The method 1200 may include steps of providing a member (e.g., a sensor member) including semiconductor material as in step 1202, and then applying heat to a surface region of the member as in step 1204 for a time, and at a temperature, sufficient to form a surface region of enhanced electrochemical activity on a semiconductor portion of the member. The treatment may be sufficient to bring about a change in electrochemical activity of greater than 2 times, greater than 5 times, or even greater than 10 times, as compared to an untreated member.

The member may be a sensor member formed from a fiber having a length substantially longer than its width and the fiber may include a semiconductor material, such as a cladding of SiC, for example. The heat may be applied as discussed above, such as by a high-power laser to a temperature in excess of 1,000° C., 1,500° C., or even 2,000° C., for example. The thus-formed electrochemically enhanced region may encompass all, or less than all, of a surface (e.g., some of a radial surface, or only one side) of the member.

In the case of the member being used in an analyte sensor, following the step of applying heat, an active region may be formed on at least a portion of the surface region of enhanced electrochemical activity as in step 1206. The step of applying the active region may be by any conventional process for applying such catalysts and/or reagents as described above.

Figure 13:
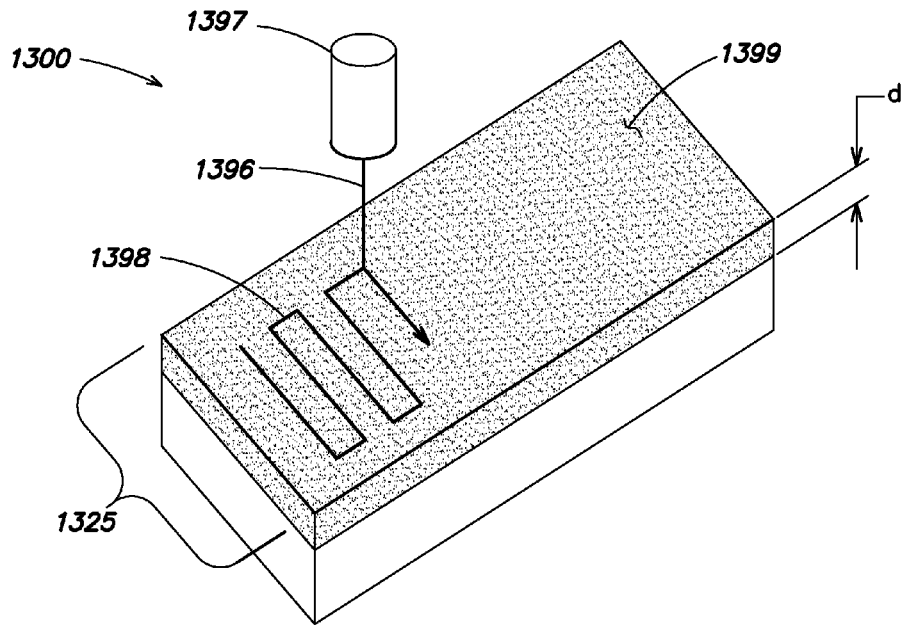
FIG. 13 is a perspective view illustrating a porous semiconductor device having a surface region of enhanced electrochemical activity surface according to the present invention.

FIG. 13 illustrates an embodiment of an electrochemically active device 1300, which may be manufactured from a semiconducting material (e.g., silicon carbide). The device 1300 may, like the members described above, include a surface region of enhanced electrochemical activity 1325, which may be thermally induced. The region 1325 may extend into the device by a depth (d) which may be less than a total thickness of the device 1300. In some embodiments, the device 1300 may be formed from a body of porous semiconducting material (e.g., a body of semiconducting porous foam). The porous foam semiconductor material may be SiC and may include a density of less than about 20%, and even between 4% and 12%, for example. As shown, the member 1300 may be formed as a panel having a thickness much less than a length or width dimension. In particular, the device 1300 may find utility as a porous electrode for an electrochemical conversion device used in an electrochemical process, such as a fuel cell or battery, for example.

A surface of the device 1300 may be made substantially more electrochemically active by subjecting a surface of the panel to heat, such as by performing a raster scan of a laser beam 1396 emanating from a laser 1397 (e.g., a YAG laser) in a path 1398 across the surface 1399 of a porous semiconducting foam panel, for example. A suitable raster scan may include repeated passes across the face of the panel, spaced at appropriate intervals such that substantially all the surface 1399 may be provided with enhanced electrochemical activity. As described above, the surface 1399 may be heated by a sufficient amount (e.g., greater than 1,000° C., greater than 1,500° C., greater than 2,000° C.) to bring about a suitable change in activity (e.g., greater than about 2 times, greater than about 5 times, or greater than about 10 times as compared to an untreated device).

Figure 14:
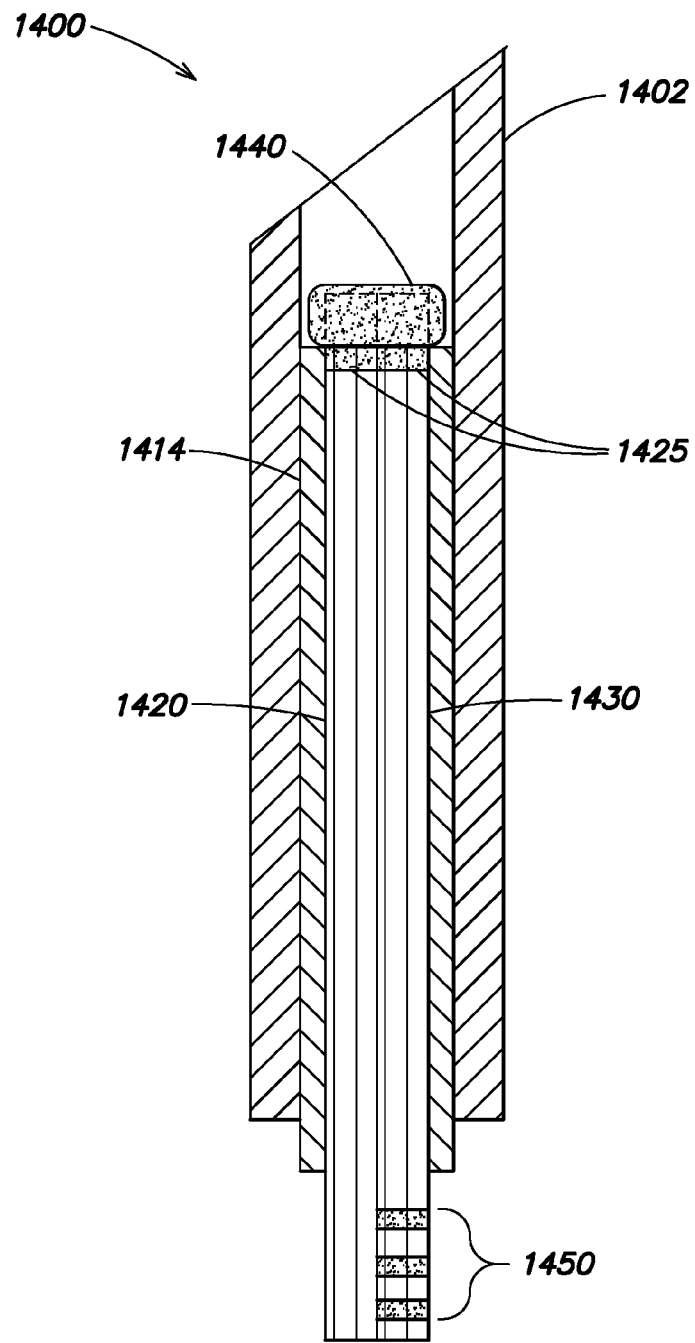
FIG. 14 is a cross-sectional side view of an exemplary embodiment of an analyte sensor provided according to the present invention.

FIG. 14 illustrates another exemplary embodiment of an analyte sensor 1400. The analyte sensor 1400 may include a first and second sensor member 1420, 1430, respectively aligned next to each other in a parallel orientation. The members 1420, 1430 may be semiconducting fibers as were described with reference to FIG. 5 and may be received within and secured in an annular sleeve 1414, which may be made of an insulating material, for example. Each of the sensor members 1420, 1430 may include a region of enhanced electrochemical activity 1425 which may be thermally induced (as described herein) and may include an active region 1440 applied over the enhanced regions 1425 which forms a bridge of material between the members 14290, 1430 at the end thereof. Of course, the first and second sensor member 1420, 1430 are otherwise electrically insulted from one another along their length. The insulation may be provided by a potting compound or a suitably thin layer of polymer insulation for example, such as a polypropylene layer, polycarbonate, polytetrafluorethylene or the like. The assembly including the members 1420, 1430 and sleeve 1414 may be received in a hollow member 1402, which may include a cleaved end forming a lancet. The hollow member 1402 may be made of a suitable rigid material, such as stainless steel tubing.

The analyte sensor 1400 provides a combined lancet and sensor apparatus, which eliminates the need to have a separate lancet as well as a user transfer of a bio-fluid to a test strip. The analyte sensor may further include a coded region 1450, which may include one or more tracks as were described with reference to FIGS. 6 and 7.

The foregoing description discloses only exemplary embodiments of devices, members, sensors, analyte sensors, apparatus including the same, and methods of manufacturing the sensors and devices of the invention. Modifications of the above disclosed devices, members, sensors, analyte sensors, apparatus including the same, and methods of manufacturing the sensors and devices, which fall within the scope of the invention, will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. A method of manufacturing an analyte sensor for measuring glucose concentration in a bio-fluid, the method comprising:
    providing a sensor member in the form of a fiber including a core formed of conductive material surrounded by a cladding formed of a semiconductor material including silicon carbide;
    providing a surface region of enhanced electrochemical activity on the cladding of the sensor member by applying heat via laser to a portion of a surface of the sensor member sufficient to alter a response to an analyte of the cladding exposed to the heat to be five or more times greater than before exposure; and
    providing an active region over at least a portion of the surface region of enhanced electrochemical activity, the active region including an agent selected from among glucose oxidase, glucose dehydrogenase (GDH), pyrolloquinoline quinine (PQQ), and flavin adenine 25 dinucleotide (FAD), and being adapted to be exposed to a bio-fluid sample.

2. The method of claim 1 wherein the laser is pulsed at between about 10 kHz and about 100 kHz.

3. The method of claim 1 wherein the laser is moved along a dimension of the sensor member at a rate of between about 20 mm/s and about 200 mm/s.

4. The method of claim 1 wherein the surface region constitutes less than all of an entire surface of the sensor member.

5. The method of claim 1 wherein the surface region constitutes substantially all of a peripheral surface of the sensor member.

6. The method of claim 1 wherein the surface region of enhanced electrochemical activity extends inwardly from the surface of the sensor member to a depth of at least 5 microns.

7. The method of claim 6 wherein the depth is at least 10 microns.

8. The method of claim 1 wherein the surface region of enhanced electrochemical activity is thermally induced by subjecting the surface region to a temperature of greater than about 1000° C. without removing a significant amount of material from the surface region.

9. The method of claim 8 wherein the temperature is greater than about 1500° C.

10. The method of claim 8 wherein the temperature is greater than about 2000° C.

11. A method of manufacturing an analyte sensor for measuring lactate concentration in a bio-fluid, the method comprising:
    providing a sensor member in the form of a fiber including a core formed of conductive material surrounded by a cladding formed of a semiconductor material, the semiconductor material including one of silicon, germanium, silicon germanide (SiGe), gallium arsenide (GaAs), and indium phosphide (InP);
    providing a surface region of enhanced electrochemical activity on the cladding of the sensor member by applying heat via laser to a portion of a surface of the sensor member sufficient to alter a response to an analyte of the cladding exposed to the heat to be five or more times greater than before exposure; and
    providing an active region over at least a portion of the surface region of enhanced electrochemical activity, the active region including lactate oxidase and being adapted to be exposed to a bio-fluid sample.

12. The method of claim 11 wherein the surface region constitutes less than all of an entire surface of the sensor member.

13. The method of claim 11 wherein the surface region of enhanced electrochemical activity is thermally induced by subjecting the surface region to a temperature of greater than about 1000° C. and wherein the cladding is formed from SiC.

14. A method of manufacturing an analyte sensor for measuring an analyte concentration in a bio-fluid, the method comprising:
    providing a rod-shaped conductive core;
    forming an annular cladding of a semiconductor material surrounding the core, the semiconductor material including one of silicon, germanium, silicon germanide (SiGe), gallium arsenide (GaAs), and indium phosphide (InP);
    forming a surface region of enhanced electrochemical activity on the cladding by applying localized heat via laser to a portion of a surface area of the cladding sufficient to alter a response to an analyte of the cladding under the surface area exposed to the localized heat to be five or more times greater than before exposure; and
    forming an active region over at least a portion of the surface region of enhanced electrochemical activity, the active region including D-aspartate oxidase and being adapted to be exposed to a bio-fluid sample.

15. The method of claim 14 wherein the surface region is less than all of an entire surface of the cladding.

16. The method of claim 14 wherein the surface region of enhanced electrochemical activity is thermally induced by subjecting the surface region to a temperature of greater than about 1000° C. and wherein the cladding is formed from SiC.

17. The method of claim 16 wherein the temperature is greater than about 1500° C.

* * * * *